United States Patent [19]

Oku

[11] 4,277,168

[45] Jul. 7, 1981

[54] ENDOSCOPE WITH MEANS FOR DETECTING ROTATION OF A DISTAL EXAMINING END

[75] Inventor: Toshio Oku, Tokyo, Japan

[73] Assignee: Machida Endoscope Co., Ltd., Tokyo, Japan

[21] Appl. No.: 27,946

[22] Filed: Apr. 6, 1979

[30] Foreign Application Priority Data

Apr. 20, 1978 [JP] Japan .............................. 53/51483[U]

[51] Int. Cl.³ .............................................. A61B 1/00
[52] U.S. Cl. ........................................ 356/138; 128/4; 350/96.26; 356/241; 356/152
[58] Field of Search ..................... 356/3, 11, 138, 372, 356/373, 241, 152; 350/96.26; 250/231 SE, 568; 128/4, 5, 6

[56] References Cited

U.S. PATENT DOCUMENTS

| | | | |
|---|---|---|---|
| 3,533,657 | 10/1970 | Da Silva | 250/568 |
| 3,730,632 | 5/1973 | Chikama | 356/3 |
| 3,826,900 | 7/1974 | Moellering | 250/568 |
| 4,078,864 | 3/1978 | Howell | 356/3 |
| 4,103,155 | 7/1978 | Clark | 250/231 SE |

Primary Examiner—R. A. Rosenberger
Attorney, Agent, or Firm—Peter L. Berger

[57] ABSTRACT

The present invention discloses an endoscope with means for detecting the direction and angle of rotation of a distal examining end. A guide tube with a mark or a porthole is provided around the distal examining end for a standard of measuring. Said mark or the porthole is counted by a pair of detecting optic bundles and optical detecting means such as, for example a photoelectric element, which are provided at the distal examining end. By these constructions, the relative rotation between the guide tube and the distal examining end is detected. Accordingly, damage to the distal examining end can be prevented.

8 Claims, 5 Drawing Figures

ENDOSCOPE WITH MEANS FOR DETECTING ROTATION OF A DISTAL EXAMINING END

BACKGROUND OF THE INVENTION

A. Field of the Invention

The present invention generally relates to an industrial endoscope, or more particularly, to an endoscope with means for detecting rotation of a distal examining end.

B. Description of the Prior Art

The endoscope was developed as a medical instrument in the beginning. But, in recent years, it is used for industrial optical detecting means. For example, the endoscope is used for inspecting the inside of a reactor pile, a jet engine or a gas tank in which man cannot gain entrance.

For the above-said optical inspection, the distal examining end with an observing window is inserted into the examining portion and the distal examining end is operated by the grip end. With more detail, a plurality of wires are stretched between the distal examining end and the grip end. The wires are rotated at the grip end in order to twist the distal examining end and the flexible sheath. Accordingly, the observing window is opposed to the object. The image of the object is transmitted from the observing window to the grip end by way of image-transmitting optic bundles, and the image can be observed by an eye or be displayed at a monitoring television which is connected to the grip end.

In the rotation mechanism with a plurality of wires, the angle of rotation of the wires at the grip end and that of at the distal examining end does not strictly correspond. Accordingly, the state of rotation at the distal examining end cannot be made out from that at the grip end. That is to say, one rotation of the distal examining end may be caused by six rotations of the wire at the grip end in the first operation. But in the next operation, only five rotations of the wire may cause one rotation of the distal examining end.

In the prior art, means for detecting the direction and angle of rotation of the distal examining end are not provided in the endoscope, so that, the state of rotation cannot be made out when changing the direction of the observing window. In addition, the distal examining end can easily be damaged by excessively rotating the distal examining end in particular direction.

SUMMARY OF THE INVENTION

Accordingly, it is an object of the invention to provide an endoscope by which rotation of the distal examining end can correctly be detected.

It is another object of the invention to provide an endoscope by which the direction of rotation of the distal examining end can correctly be detected.

It is a further object of the invention to provide an endoscope by which the angle of rotation of the distal examining end can correctly be detected.

It is another object of the invention to provide an endoscope by which the damage to the distal examining end can be prevented.

To achieve the objects, a guide tube with a mark or a porthole is provided around the distal examining end for the standard of measuring. Said mark or the porthole is counted by a pair of detecting optic bundles and optical detecting means such as, for example a photoelectric element, in order to detect the relative rotation between the guide tube and the distal examining end.

The above and further objects and novel features of the invention will more fully appear from the following detailed description when the same is read in connection with the accompanying drawings. It is to be expressly understood, however, that the drawings are for purpose of illustration only and are not intended as a definition of the invention.

DETAILED DESCRIPTION OF THE PREFERRED EMBODIMENT

Figure 1:
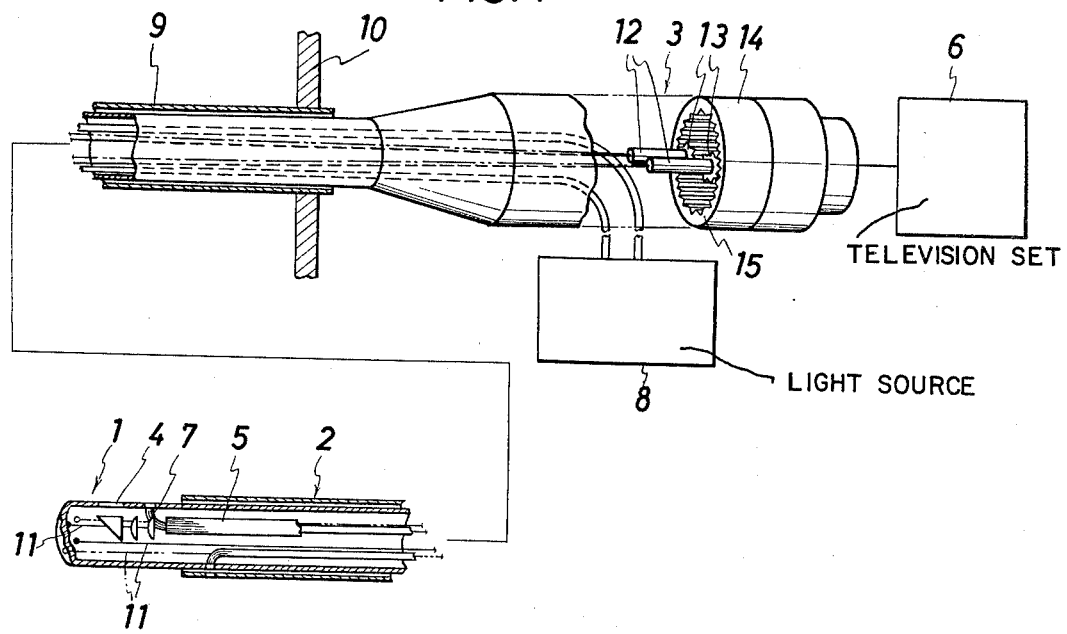
FIG. 1 is a schematic illustration showing an endoscope according to an embodiment of the invention.

In FIG. 1, numeral 1 indicates a distal examining end of an endoscope, numeral 2 indicates a flexible sheath and numeral 3 indicates a grip end. In the distal examining end 1, an observing window 4 is provided for transmitting an image of the object to the grip end 3 by way of image-transmitting optic bundles 5. The object, such as a crack, can be observed by a monitoring television set 6 which is connected to the grip end 3. Numeral 7 indicates a light guide for illuminating the object by a light from a light source 8. Numeral 9 indicates a guide tube, one end of which may be fixed to a wall 10 of a reactor pile and the endoscope is guided by the guide tube 9. That is to say, the endoscope is slidable to the guide tube 9.

When observing the object by the endoscope, it is necessary to change the position of the observing window 4 for definitely catching the object within the visual field. The distal examining end 1 should be moved forward or rearward or be rotated for the observation. The forward and rearward movement is effected by changing the whole position of the endoscope. But, it is necessary to twist wires 11 for rotating the distal examining end 1. A plurality of wires 11 are stretched between the distal examining end 1 and the grip end 3 via the flexible sheath 2. The forward end of the wires 11 are attached to the wall of the distal examining end 1 and the rearward end to a rotor 12 of the grip end 3. A gear 13 is provided at one end of the rotor 12 and the gear 13 is engaged with an inside gear 15 of a ring 14. Said ring 14 can be rotated by hand or by a drive mechanism (not shown). The rotation force of it rotates the wires 11 via the inside gear 15 and the gear 13 and renders torsional force to the wires 11. The distal examining end 1 and the flexible sheath 2 is rotated by the torsional force of the wires 11 and the position of the observing window 4 can be changed. Thereby, the observing window 4 can be correctly positioned opposed to the object.

By the way, as described before, the rotation mechanism of the distal examining end 1 by the wires 11 has a defect that there are discrepancies between the angle of rotation at the grip end 3 and that of at the distal examining end 1. Namely, in the first operation, one rotation of the distal examining end 1 can be obtained by six rotations of the ring 14. But in the next operation, one rotation of the distal examining end 1 may be obtained by five rotations of the ring 14. This rule applies to the case when the ring 14 is reversed. Accordingly, errors of rotation are gathered and the state of rotation at the distal examining end 1 cannot be made out. For all these defects, the rotation mechanism by the wires 11 is simple in its construction.

To solve the problem, a guide tube 9 with a mark or a porthole is provided around the distal examining end 1 for a standard of measuring. The relative rotation between the guide tube 9 and the distal examining end 1 is optically detected in order to acknowledge the direction and the angle of rotation of said distal examining end 1.

Figure 2:
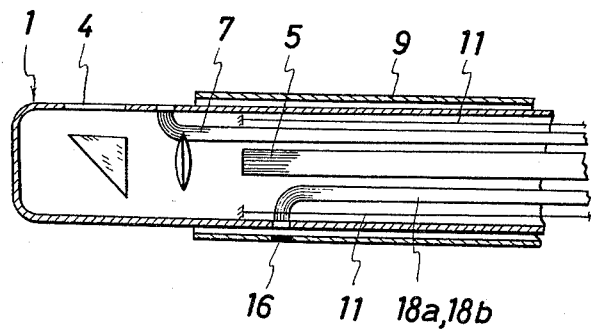
FIG. 2 is a partial cross-sectional view showing the distal examining end of FIG. 1.
Figure 3:
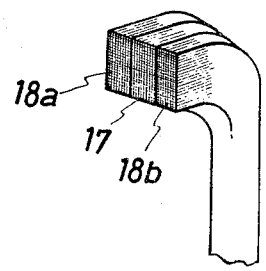
FIG. 3 is a illustration showing the detecting optic bundles of FIG. 2.

In FIG. 2, numeral 16 indicates a mark which is provided at the inside of the guide tube 9. One or a plurality of the marks 16 may be provided, fixing a specific point of the inside as a starting point. A dot, a line, a number or a bar code may be used for the mark 16. In order to optically detect the mark 16, a pair of detecting optic bundles 18a, 18b are provided at both sides of an illuminating light guide 17 at the distal examining end 1, as shown in FIG. 3. The rear end of the illuminating light guide 17 is connected to the light source 8. The rear end of said detecting optic bundles 18a, 18b are connected to a detector circuit (not shown) which comprises a photoelectric element, up-down controller and a counter and so on.

The operation of above-said embodiment will be described herein-under. When the distal examining end 1 is rotated by twisting the wires 11 with the ring 14 of the grip end 3, a reflection of the mark 16 which is illuminated by a light from the light guide 17 is introduced to the detector circuit by way of the detecting optic bundles 18a, 18b. The result is displayed on the monitoring television 6. Accordingly, the direction and the angle of rotation of the distal examining end toward the guide tube 9 can be acknowledged, notwithstanding the rotation of the ring 14. The direction of the rotation can be acknowledged according to the fact that which of the detecting optic bundles 18a, 18b at first detects the mark 16. Also, the angle of rotation can be acknowledged by reading the mark 16 inside the guide tube 9 which is shown as a bar code. The term "angle of rotation" includes the number of rotation.

Figure 4:
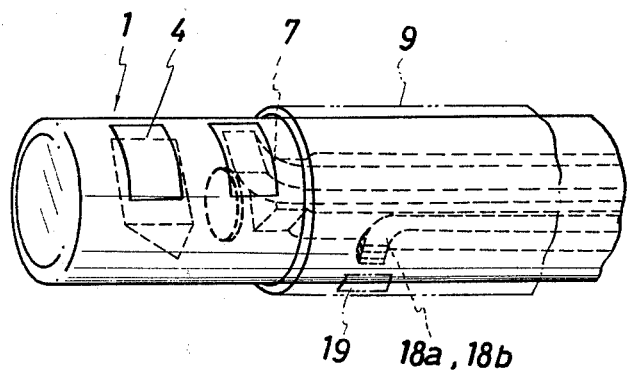
FIG. 4 is a perspective view showing the distal examining end according to another embodiment of the invention.

Another embodiment is shown in FIG. 4. In the figure, numeral 19 indicates a porthole which is provided at the guide tube 9. Numerals 18a, 18b indicate the detecting optic bundles. In the embodiment, the light from the porthole 19 is detected by said detecting optic bundles 18a, 18b, therefore, the illuminating light guide is not necessary. One or a plurality of the portholes 19 may be provided at predetermined intervals around the guide tube 9. And, if necessary, the dimension of the porthole 19 may be changed in order to vary the quantity of light. By this embodiment, the direction of rotation of the distal examining end can be acknowledged according to the fact that which of the detecting optic bundles 18a, 18b at first detects the light from the porthole 19. In addition, the angle of rotation of the distal examining end 1 can be acknowledged according to the number that the porthole 19 is detected. In these embodiments, a photoelectric element may be directly provided at the distal examining end 1 and an electric signal may be fed to the detector circuit by way of a lead wire, without using the optic bundles 18a, 18b.

Figure 5:
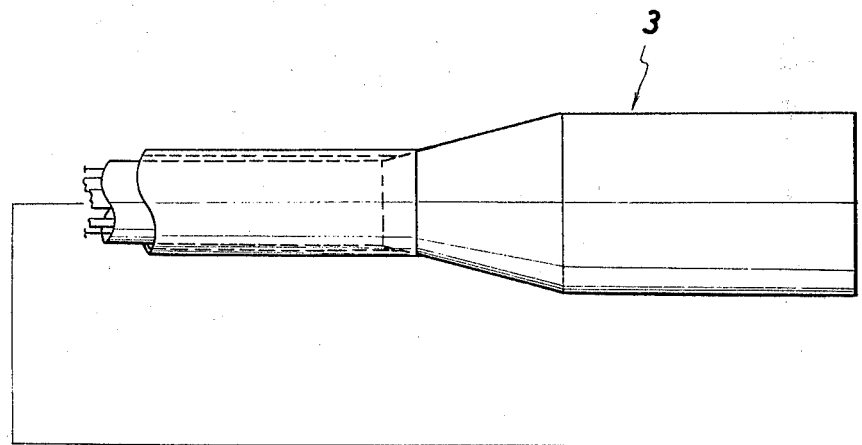
FIG. 5 is a schematic illustration showing an endoscope according to a further embodiment of the invention.
Figure 5:
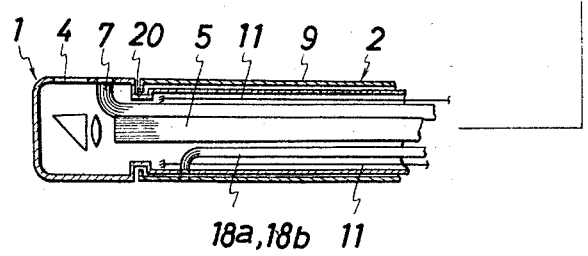

In FIG. 5, the rear end of the guide tube 9 is connected to the grip end 3 and the forward end is inserted in a groove 20 at the distal examining end 1. The distal examining end 1 and the flexible sheath 2 can be rotated toward the grip end 3.

As is described in detail, the endoscope according to the present invention detects the relative rotation between the guide tube and the distal examining end, setting the guide tube for the standard of measuring. Accordingly, the direction of the visual field can be confirmed. In addition, the damage to the distal examining end can be prevented.

While there have been shown and described and pointed out the fundamental novel features of the invention as applied to preferred embodiments. It will be understood that the various omissions and substitutions and changes in the form and details may be made by those skilled in the art without departing from the spirit of the invention.

What is claimed is:

1. An endoscope having a grip end and a distal examining end and means for observing what is viewed at said distal examining end,
   said distal examining end being capable of being rotated under control from said grip end, an improvement comprising
   a guide tube extending along said endoscope through which said endoscope passes,
   said guide tube having a distal end proximately located to said distal examining end,
   said guide tube being fixed and having no rotation imparted thereto, and
   optical measuring means integrally formed at said distal end of said guide tube for optically measuring the amount of rotation imparted to the distal examining end of said endoscope.

2. An endoscope according to claim 1 comprising a measuring standard located at the distal end of said guide tube, a light guide for illuminating the mark, a pair of detecting optic bundles at both sides of the light guide, and a detector circuit which receives signals from said detecting optic bundles to indicate the amount of said rotation.

3. An endoscope according to claim 2, wherein said measuring standard comprises marks on the inside of said guide tube.

4. An endoscope according to claim 3, wherein said mark comprises a bar code.

5. An endoscope according to claim 1, comprising a porthole at the distal end of said guide tube, detecting optic bundles carried in said endoscope having distal ends thereof proximate to said porthole, with light at the distal examining end entering said porthole to be detected by said detecting optic bundles to measure said rotation.

6. An endoscope according to claim 1, wherein said optical measuring means comprises a photoelectric element at the distal examining end, and means formed with said guide tube to vary the amount of light received by said photoelectric element as said distal examining end rotates.

7. An endoscope according to claims 2 or 6, wherein the rear end of the guide tube is connected to the grip end and the distal end is inserted in a groove at the distal examining end of said endoscope.

8. An endoscope according to claim 1, 2 or 6, wherein said guide tube is fixedly connected to said grip end to prevent rotation of said guide tube when said distal examining end rotates.

* * * * *